(12) United States Patent
Gündel

(10) Patent No.: US 7,680,313 B2
(45) Date of Patent: Mar. 16, 2010

(54) METHOD AND APPARATUS FOR POST-PROCESSING OF A 3D IMAGE DATA RECORD, IN PARTICULAR FOR VIRTUAL COLONOGRAPHY

(75) Inventor: Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 840 days.

(21) Appl. No.: 11/527,614

(22) Filed: Sep. 27, 2006

(65) Prior Publication Data

US 2007/0073114 A1 Mar. 29, 2007

(30) Foreign Application Priority Data

Sep. 28, 2005 (DE) .................. 10 2005 046 385

(51) Int. Cl.
*G06K 9/00* (2006.01)
*A61B 5/00* (2006.01)
(52) U.S. Cl. ...................... 382/131; 600/300
(58) Field of Classification Search ................ 382/128, 382/129, 130, 131, 132, 133, 134, 199, 260–266; 378/4, 21–27, 46, 90, 92, 98.4, 98.6, 98.9, 378/101, 140, 901; 600/300, 407, 425, 435; 424/1.11; 128/920, 925
See application file for complete search history.

(56) References Cited

U.S. PATENT DOCUMENTS

| | | | | |
|---|---|---|---|---|
| 5,594,767 | A * | 1/1997 | Hsieh | 378/8 |
| 6,331,116 | B1 * | 12/2001 | Kaufman et al. | 434/262 |
| 6,366,800 | B1 * | 4/2002 | Vining et al. | 600/425 |
| 2003/0223627 | A1 | 12/2003 | Yoshida et al. | |
| 2004/0052328 | A1 | 3/2004 | Sabol et al. | |
| 2005/0107691 | A1 | 5/2005 | Zalis | |
| 2005/0190984 | A1 | 9/2005 | Fischer et al. | |

OTHER PUBLICATIONS

M.E. Zalis et al. : "Digital Subtraction Bowel Cleansing for CT Colonography Using Morphological and Linear Filtration Methods",IEEE Transactions on Medical Imaging, vol. 23, No. 11, 2004, pp. 1335-1343.
Stephen L. Ristvedt et al.: "Patient Preferences for CT Colonography, Conventional Colonoscopy, and Bowel Prepara", The American Journal of Gastroenterology, vol. 98, No. 3, 2003, pp. 578-585.
M.E. Zalis et al. : "CT Colonography: Digital Subtraction Bowel Cleansing with Mucosal Reconstruction—Initial Observations", Radiology, vol. 226, No. 3, pp. 911-917, 2003.

\* cited by examiner

*Primary Examiner*—Abolfazl Tabatabai
(74) *Attorney, Agent, or Firm*—Harness, Dickey & Pierce, P.L.C.

(57) ABSTRACT

A method is disclosed for post-processing of a 3D image data record which has been recorded by way of an imaging tomographic appliance of a body area, and covers at least one hollow organ which is at least partially filled with contrast agent. An imaging apparatus is also disclosed. In the method, an automatic three-dimensional edge detection process is carried out in the 3D image data record in order to determine transitions between areas which have contrast agent and a wall of the hollow organ as boundary surfaces. A weighted high-pass filtering process is carried out at right angles to the boundary surfaces and leads to removal of the areas which have contrast agent and in which process areas around the transitions are given a lower weighting than areas which are further away from the transitions. After low-pass filtering in the areas around the transitions, a 3D image data record is produced from which the areas which are filled with contrast agent are eliminated, without image artifacts being produced at the transitions to the wall of the hollow organ. The method can be used in particular for virtual bowel cleaning in virtual colonography.

28 Claims, 3 Drawing Sheets

METHOD AND APPARATUS FOR POST-PROCESSING OF A 3D IMAGE DATA RECORD, IN PARTICULAR FOR VIRTUAL COLONOGRAPHY

PRIORITY STATEMENT

The present application hereby claims priority under 35 U.S.C. §119 on German patent application number DE 10 2005 046 385.1 filed Sep. 28, 2005, the entire contents of which is hereby incorporated herein by reference.

FIELD

The present invention generally relates to a method for post-processing of a 3D image data record which has been recorded, for example, via an imaging tomographic appliance of a body area, and which covers at least one hollow organ which is at least partially filled with contrast agent. The invention also generally relates to an apparatus for recording of a 3D image data record of a body area of a patient, for example a computer tomography (CT) or magnetic resonance tomography (MR) system. It may relate to one which has at least one image processing module for carrying out the method.

One major field of application of at least one embodiment of the present method and of the associated apparatus is the field of virtual colonography.

BACKGROUND

Bowel cancer represents one frequent cause of death in the western nations. One good initial indicator of this illness is polyps which are formed in the bowel quite a long time before the outbreak of bowel cancer itself. In many cases, these develop over several years to form malignant carcinomas.

One effective measure for combating bowel cancer is thus early identification of polyps. Endoscopic methods have been used in the past for this purpose. Recently, the technique of virtual colonography has been becoming increasingly important, in which the bowel is scanned by way of computer tomography or magnetic resonance tomography and the images obtained in the process are then analyzed at medical workstations.

In the case of both techniques, colonoscopy by way of an endoscope and virtual colonography, the bowel must be cleaned by suitable medication before the examination, in order to allow structures which indicate polyps to be identified on the bowel wall. Patients consider this to be unpleasant, and this frequently forms an impediment to carrying out this examination.

In one known method for virtual colonography, the patient is fed with a low-fiber diet for one or two days before the examination, supplemented with a marking contrast agent which can be identified well in the imaging process. In this case, barium or gastrografin are predominantly used for computer tomography. The marking contrast agent mixes to a greater or lesser extent with stool or liquid residues in the bowel, and can thus be identified directly in the subsequently recorded medical images.

In order to achieve better contrast on the bowel wall during the examination, a so-called basic contrast agent (for example air or $CO_2$ in the case of CT, water in the case of MR) is added. During post-processing of the image data, the stool marking contrast agent and liquid marking contrast agent mixtures are then identified using a threshold-value process, and are eliminated from the one or more images by digital subtraction. Bowel cleaning initiated by medication need no longer be carried out, or need be carried out only to a restricted extent, with this technique, which is also referred to as virtual bowel cleaning.

The high contrast difference between the air-filled bowel and the surrounding bowel wall is imaged by the imaging processes used onto a transition over a plurality of pixels or voxels in the 2D or 3D image produced in this case. This may be due to partial volume artifacts or to the transfer function. However, the subtraction process that is carried out for virtual bowel cleaning leads to imaging errors in particular at the transitions between areas which have marking contrast agent and the bowel walls, which have a similar structure to the polyps that are being looked for, thus making it difficult or even impossible to identify them.

An improved method for virtual bowel cleaning takes account of these transitions and uses a filter mask to carry out a different subtraction process within the areas filled with contrast agent and at the transition to the bowel wall. In this method, which is described in more detail for example in M. E. Zalis et al., "Digital Subtraction Bowel Cleansing for CT Colonography Using Morphological and Linear Filtration Methods" IEEE Transactions on Medical Imaging, Vol. 23, No. 11, 2004, pages 1335 to 1343, the transition to the bowel wall is modeled again after subtraction of the areas filled with marking contrast agent.

In this case, an edge detection process is carried out in each of the axial 2D image data records, in order to detect the sharp transitions that result after the subtraction process. These transitions are then replaced by a smoother falling transitional area, as can normally be seen in CT images at the transition between the bowel wall and the air-filled bowel. These newly modeled transitions are then low-pass filtered in order to carry out a final smoothing process. The entire method is carried out in two dimensions, that is to say with the individual 2D slice images.

SUMMARY

At least one embodiment of the present invention is directed to a method and/or an imaging apparatus, which offer a further capability for post-processing of tomographic image data of an examination area in order to allow areas filled with marking contrast agent to be eliminated from the images, without disturbing image artifacts. In this case, the method and the system are intended to be suitable, in particular, for virtual bowel cleaning in the field of virtual colonography.

In the present method of at least one embodiment for post-processing of a 3D image data record, which has been recorded by way of an imaging tomographic appliance, in particular a CT scanner or a magnetic-resonance scanner, of a body area, and which covers at least one hollow organ which is at least partially filled with marking contrast agent and with basic contrast agent, an automatic three-dimensional edge detection process is carried out at least in one section of the image data record of interest, in order to determine at least transitions between areas which have marking contrast agent and the wall of the hollow organ in the image data record as boundary surfaces. After this determination process, a weighted high-pass filtering process is carried out at right angles to the boundary surfaces in the entire image data record or the section of interest and leads to elimination of the areas which have contrast agent and in which process areas around the transitions are given a lower weighting than areas which are further away from the transitions. In this context, illumination should be understood as meaning that these areas subsequently appear in the image as if they have not been filled with liquid or marking contrast agent. A low-pass filtering process in then also carried out in the areas around the transitions, in order to smooth the transitions.

Transitions between areas having marking contrast agent and areas contain basic contrast agent, and between areas also containing basic contrast agent and the wall of the hollow organ are preferably determined as boundary surfaces in the image data record during the three-dimensional edge detection process, so that these transitions are also subsequently smoothed, possibly differently. This relates in particular to transitions between the three media, that is to say transitions at which an area having marking contrast agent, an area containing basic contrast agent and the wall of the hollow organ coincide.

An embodiment of the present method includes a three-dimensional method for post-processing of a 3D image data record, in which a three-dimensional edge detection process and high-pass filtering as well as low-pass filtering are carried out. The weighted high-pass filtering process results in the transition between areas which were originally filled with marking contrast agent and the wall of the hollow organ or the areas filled with basic contrast agent (for example air) being reproduced without disturbing image artifacts in the display of the postprocessed image data. In this case, an embodiment of the present method is particularly suitable for virtual bowel cleaning for virtual colonography, in order to allow the images to be analyzed without disturbing image artifacts at the transitions to the bowel wall.

At least one embodiment of the method can be applied to the entire 3D image data record. In one advantageous refinement of an embodiment of the method, however, the area to be filtered is initially restricted to the section of interest, in order to reduce the complexity. For this purpose, the hollow organ is first of all segmented in the 3D image data record on the basis of the values of the area having contrast agent. However, since parts of the wall of the hollow organ are also required for the subsequent filtering step, the segmentation result has a specific area added to it around the area that is filled with contrast agent. This step is also advantageous when the segmentation process cannot successfully process parts of the interior of the hollow organ because of an inhomogeneous contrast agent distribution.

The method that is used in at least one example embodiment as the method for three-dimensional edge detection in the 3D image data record is one in which variances are calculated in a predetermined area or radius around the image voxel for each voxel in the image data record or in the section of interest of the image data record, referred to in the following text as an image voxel, in order to determine sudden contrast changes and their spatial orientation, as well as their tangential planes T in the 3D image data record of section of interest, as boundary surfaces.

In a first advantageous embodiment, one-dimensional variances can in this case be calculated for at least three spatial directions, three of which spatial directions are linearly independent. In this case, it is advantageous for the large number of spatial directions for which one-dimensional variances are calculated to be arranged distributed as uniformly possible in space. A distribution which is as uniform as possible can be achieved, for example, by using canonic axes and/or surface diagonals and/or spatial diagonals of any desired cuboid reference volume in the section of interest or in the image data record as spatial directions. If all of the axes mentioned above are used, then this results in a total number of 13 spatial directions, with three canonic axes, six surface diagonals and four spatial diagonals. In this case, it should also be noted that the cuboid reference volume can arranged in any desired manner in space, preferably using a cube since this does not result in any preferred directions.

The spatial orientation of a sudden contrast change can be determined by way of the tangential plane, with this plane being covered by the vectors $v_{min}$ and $v_\perp$, with the vector $v_\perp$ once again being at right angles to the plane which is covered by the vectors $v_{min}$ and $v_{max}$, and with the vector $v_{max}$ pointing in the direction of the greatest magnitude of the variance, and with the vector $v_{min}$ pointing in the direction of the smallest magnitude of the variance.

In addition to embodiment of the method in which one-dimensional variances are calculated, an embodiment of a method is also possible which calculates two-dimensional variances on at least three planes, two which are linearly independent. In this case, in a similar manner to that already described, the large number of planes on which the two-dimensional variance is calculated should be aligned such that their normal vectors are distributed as uniformly as possible in space since this results in all of the spatial directions being considered uniformly.

Furthermore, it is preferable to use planes over which the two-dimensional variances are determined whose normals correspond to the canonic axes and/or surface diagonals and/or spatial diagonals of any desired cuboid reference volume in the examination area. In this case, the plane which is preferably chosen as the tangential plane is that which has the least two-dimensional variance.

Finally, in this embodiment of a two-dimensional method as well, one-dimensional variances can be determined in different directions on the tangential plane T and, from this, the direction of minimum variance $v_{min}$ and the perpendicular $V_\perp$ to this can be determined, in which, by definition, the perpendicular $v_\perp$ is assumed to be the direction of maximum one-dimensional variance $V_{T,max}$ on the tangential plane. Conversely, one-dimensional variances can also be determined on the tangential plane in different directions and, from this, the direction of maximum variance on the plane $v_{max}$ and the perpendicular $v_\perp$ to this can be determined, in which case, by definition, the perpendicular $v_\perp$ is assumed to be the direction of minimum one-dimensional variance $V_{T,min}$ on the tangential plane.

The tangential planes determined in this way result, together, in the sought boundary surfaces. A suitable weighting process is carried out for the subsequent high-pass filtering process, which is carried out three-dimensionally at right angles to the boundary surface or tangential planes, in which the areas of the transitions between the area filled with marking contrast agent and the cavity wall or the area filled with basic contrast agent are given a lower weighting than the areas which are further away. The different weighting is in this case carried out by way of a weighting function which ensures a soft transition between the more heavily weighted areas and the less heavily weighted areas.

An example embodiment of the present apparatus, a medical tomography system, in particular a CT or MR system, has, as is known, an image recording system for recording of measurement data as well as an image processing system for the reconstruction of a 3D image data record from the measurement data. The image processing system in the case of an embodiment of the present invention has a program module which carries out the method steps of post-processing according to an embodiment of the present method, on an automated basis.

BRIEF DESCRIPTION OF THE DRAWINGS

Embodiments of the present method and the associated apparatus will be explained once again briefly in the following text on the basis of one example embodiment and in conjunction with the drawings, without any restriction to the scope of protection governed by the patent claims. In this case:

DETAILED DESCRIPTION OF THE EXAMPLE EMBODIMENTS

Figure 1:
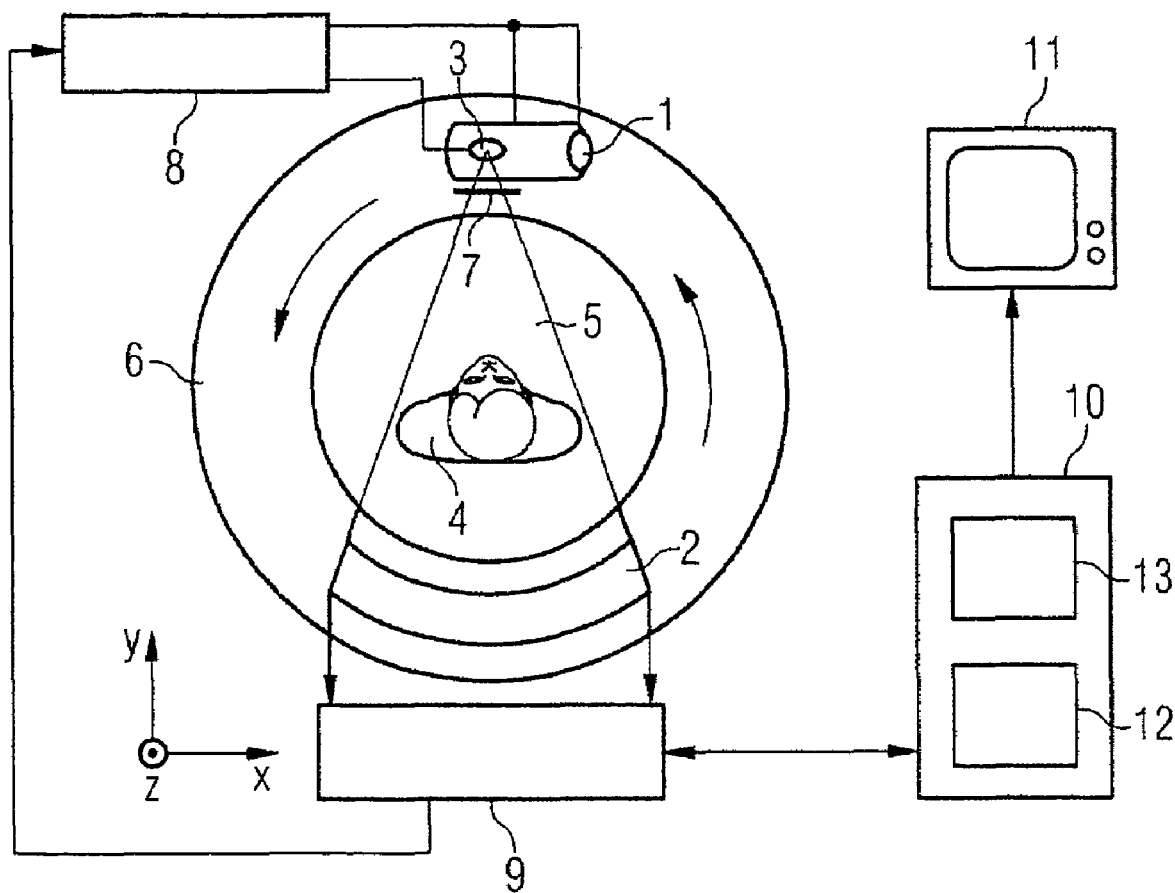
FIG. 1 shows a highly schematic illustration of a CT system according to an embodiment of the present invention.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows, highly schematically, one configuration of a computer tomography system designed according to an embodiment of the present method. The computer tomography system has an X-ray source in the form of an X-ray tube 1, which emits a fan-shaped X-ray beam 5 in the direction of a detector row having X-ray detector elements 2. Both the X-ray tube 1 and the detector elements 2 are arranged on a rotating frame 6, the so-called gantry, which rotates continuously around a patient 4 during a measurement.

The patient 4 lies on a patient couch, which is not illustrated in FIG. 1 but extends into the gantry 6. The gantry 6 rotates on an x-y plane. in a Cartesian coordinate system x-y-z, which is indicated in FIG. 1. The patient couch can move along the z axis, which corresponds to the slice thickness direction of the respective slices of the patient 4 to be displayed. The extent of the X-ray beam 5 in the z direction, in the present illustration the direction at right angles to the plane of the drawing, is predetermined on the one hand by the extent of the focus 3 on the rotating anode of the X-ray tube 1, and on the other hand by the screen 7 which is arranged at the tube end and whose screw opening can be adjusted in the z direction.

The X-ray tube 1 is supplied with a high voltage of, for example, 120 kV from a high-voltage generator 8. A controller 9 is used to drive the individual components of the CT scanner, in particular the high-voltage generator 8, the gantry 6, the detector elements 2 as well as the patient couch, in order to record the measurement data. The measurement data produced by the detectors 2 is passed to an image computer 10. The image computer has an image reconstruction unit 12 in which the image is reconstructed, in the present example with the 3D image data record being reconstructed from the measurement data. The views of the 3D image data record chosen by the user can be displayed on a monitor 11.

Figure 2:
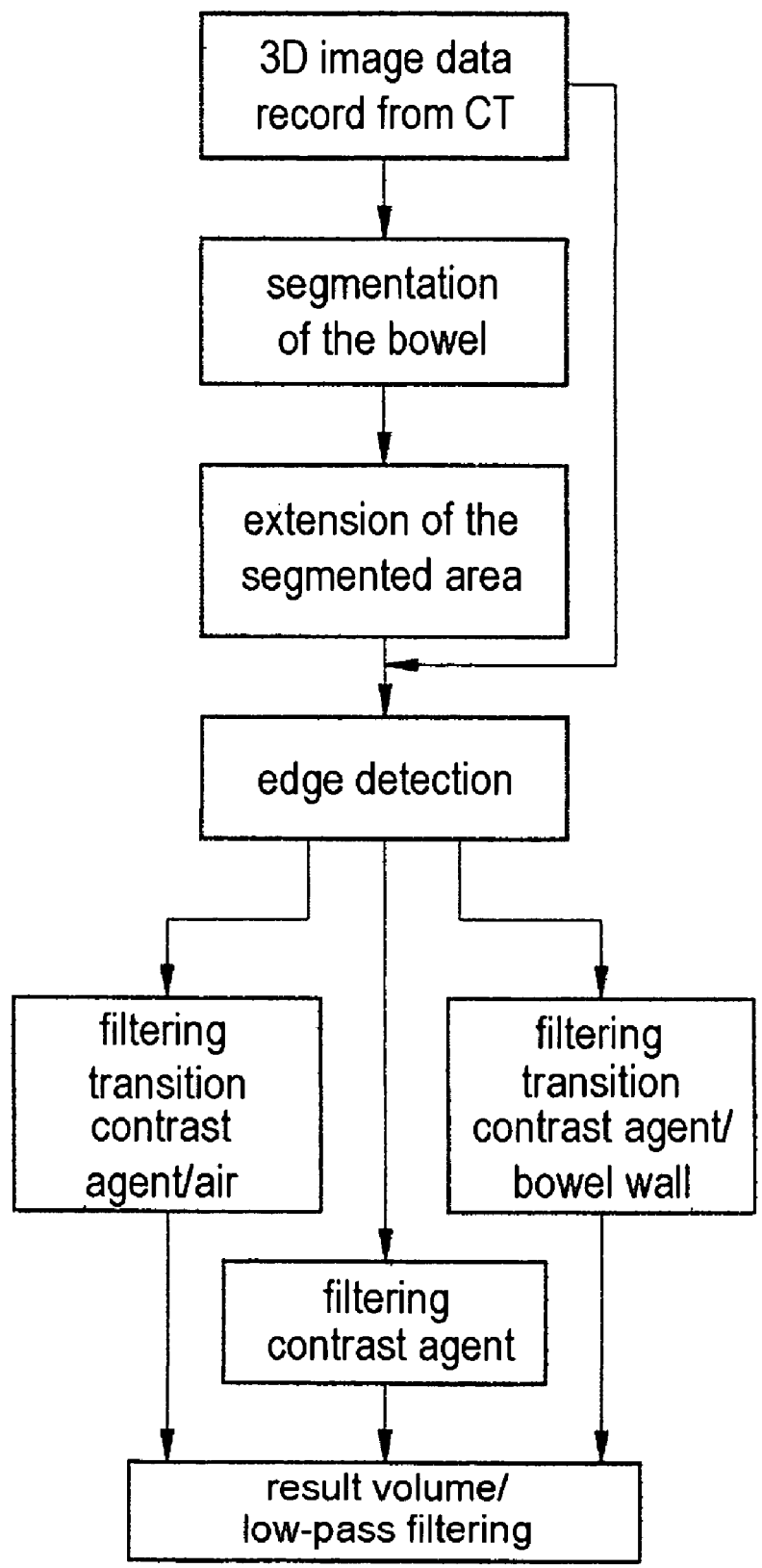
FIG. 2 shows, schematically, one example of the method procedure for an embodiment of the present method.

Computer tomography systems such as these are familiar to those skilled in the art. In the case of the present computer tomography system, the image reconstruction unit 12 is followed by an image post-processing unit 13 which automatically postprocesses the resultant 3D image data record as required, that is to say on request by the user, in accordance with the present method, as is illustrated by way of example in FIG. 2.

In this example, in which a virtual colonography is carried out with virtual bowel cleaning, the patient will have consumed food enriched with marking contrast agent over a time period of 1 to 2 days prior to the examination. Once air has been blown into the bowel as the basic contrast agent, the CT scanner records a 3D image data record of the body area of the patient surrounding the bowel. Once the 3D image data record has been reconstructed, the bowel is segmented in the image post-processing unit 13 on the basis of the CT values of the area filled with contrast agent in the 3D image data record.

The CT values of this area which is filled with contrast agent are in the range between 300 and 500 HU (Hounsfield Units) depending on the contrast agent used, so that this area can be separated easily from the other image areas by way of a threshold-value process. By way of example, the CT values of fat components are thus in the region of −20 HU, while those for the bowel wall are in the range from about 10 to 20 HU. Air-filled bowel areas have CT values of −1000 HU. Following this threshold-value-based segmentation process on the area filled with the contrast agent, this area is extended in all directions in order in this way also to include the bowel wall in the segmented area.

Figure 3:
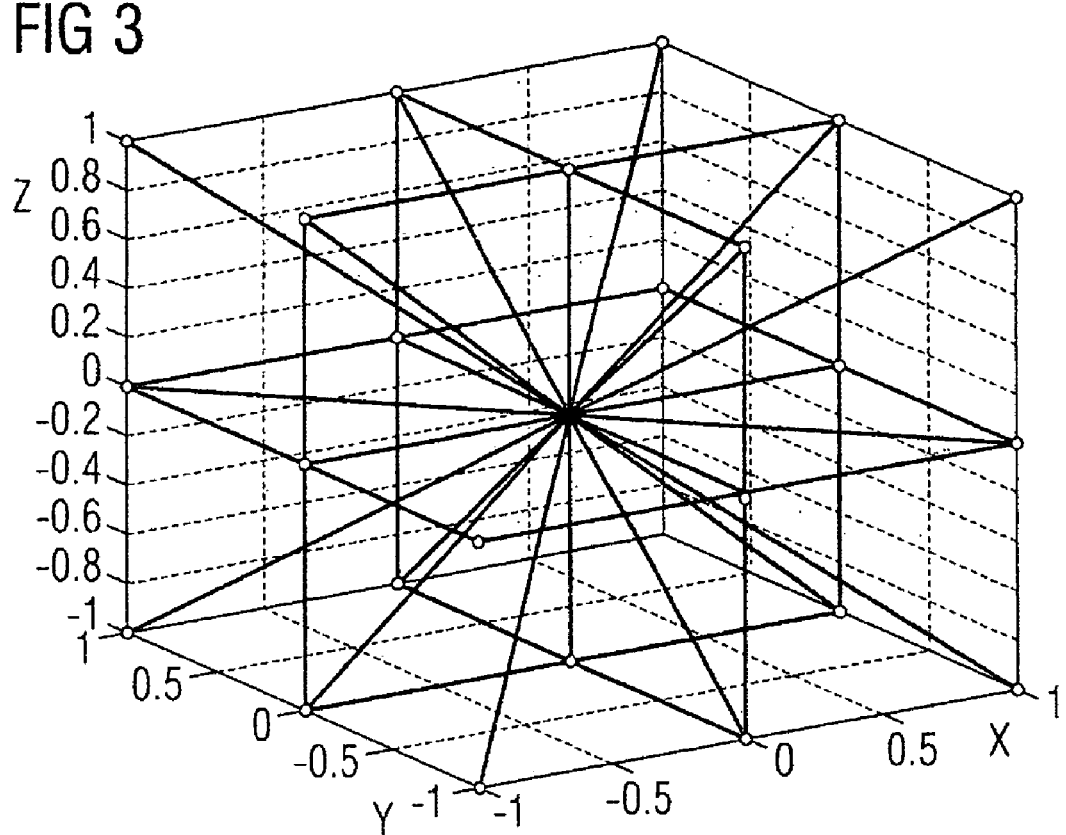
FIG. 3 shows an illustration of selected directions for variance calculation for 3D edge detection.

This segmented section of the image data record is then processed further using the present method. In this case, a three-dimensional edge detection process is carried out, including the determination of tangential planes based on variances in 13 spatial direction. For this purpose, one-dimensional variances are calculated in a suitable radius R for these spatial directions for each image voxel, which represents a data point in the three-dimensional space of the examination object, with coordinates x, y, z. FIG. 3 shows one sensible choice for these spatial reactions. In this case, the figure shows the three canonic axes, the six surface diagonals and the four spatial diagonals, that is to say a total of 13 preferred directions, within a cube of edge length 1. These 13 preferred spatial directions that are illustrated result in a largely isotropic distribution of the directions in the three-dimensional space, without any particular preferred orientation.

A similarly uniform distribution could also be achieved by placing an equilateral polyhedron around the point under consideration such that it forms the geometric centroid of the polyhedron, in which case the connecting lines from the geometric centroid to the corner points can act as preferred, uniformly distributed, spatial directions.

The area under consideration, with the radius R over which the linear variances are calculated is preferably chosen to be in the same order of magnitude as the correlation length of the high-pass filter which is applied to the image data in a subsequent method step.

Figure 4:
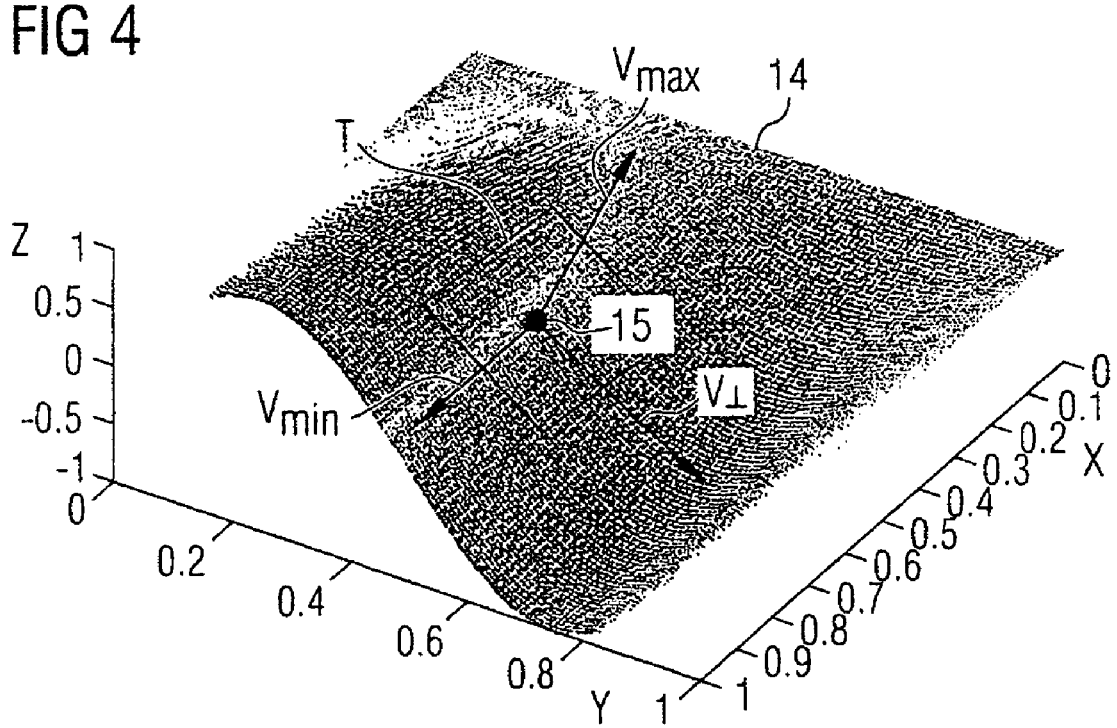
FIG. 4 shows one example embodiment of a tangential plane for edge detection.

If a directional sudden contrast change or an edge occurs locally, then the distribution of the one-dimensional variances from the previous step is designed such that the magnitude is at a maximum for that direction $v_{max}$ which is at right angles to the edge in the three-dimensional space. The plane at right angles to the selected direction is thus the tangential plane T to the edge. FIG. 4 shows one such tangential plane T in a detailed image of an object. The two-dimensional contour of this three-dimensional object with the same CT values is in this case displayed as a boundary surface 14, on which one image voxel 15 and its surrounding area are considered. Starting from this image voxel 15, the direction of the greatest measured linear variance $v_{max}$ and the direction of the least measured linear variance $v_{min}$ are shown, with the tangential plane T being covered by the perpendicular $v_\perp$ to $v_{min}$ and $v_{max}$, and the vector $v_{min}$.

This determination of the tangential plane T is carried out for each individual image voxel in the segmented area. The tangential planes determined during this process result in the sought boundary surface between the area which is filled with contrast agent and the bowel wall.

After the determination of these boundary surfaces or edges, a high-pass filtering process is carried out, in which the edge transition is taken into account in such a manner that less filtering is carried out at the edge, and greater filtering further away from the edge in the area that is filled with marking contrast agent (the marking contrast agent mixture in the bowel). This leads to a subtraction process being carried out within the marking contrast agent mixture in the area which is filled with the marking contrast agent, such that this area is eliminated from the image data, and appears dark in the CT image. This weighted high-pass filtering can also be carried by subtraction of the marking contrast agent and subsequent low-pass filtering at the edge. Because the transition for the different weighting for the high-pass filtering is chosen to be smooth, this filtering does not result in any sharp contrast transitions. In the same way, filtering with a lower weighting is carried out at the transition between the areas which are filled with marking contrast agent and the areas which are filled with air.

The transitions between the inner areas of the marking contrast agent mixture and the edges to the air-filled bowel interior, as well as to the bowel wall, are still inhomogenous after this high-pass filtering, and are thus smoothed by way of a low-pass filter. The result is a post-processed 3D image data record from which the marking contrast agent mixture has been eliminated, without the creation of disturbing image artifacts at the transitions to the bowel wall.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following

What is claimed is:

1. A method for post-processing of a 3D image data record of at least one hollow organ which is at least partially filled with marking contrast agent and with basic contrast agent, recorded via an imaging tomographic appliance, the method comprising:
   carrying out an automatic three-dimensional edge detection process, at least in one section of the image data record of interest and covering the hollow organ which is filled with contrast agent, to determine at least transitions between areas including marking contrast agent and one wall of the hollow organ in the image data record as boundary surfaces;
   carrying out a weighted high-pass filtering process at right angles to the boundary surfaces and leads to removal of the areas including contrast agent, process areas around the transitions being given a relatively lower weighting than areas relatively further away from the transitions; and
   carrying out a low-pass filtering process in the areas around the transitions, to smooth the transitions.

2. The method as claimed in claim 1, wherein, during the three-dimensional edge detection process, transitions between areas including marking contrast agent and areas containing basic contrast agent, between areas containing basic contrast agent and the wall of the hollow organ, and between areas containing basic contrast agent and the wall of the hollow organ, are also determined as boundary surfaces in the image data record.

3. The method as claimed in claim 1, wherein the hollow organ in the 3D image data record is segmented in order to obtain the section of interest in the image data record for the automatic three-dimensional edge detection process.

4. The method as claimed in claim 3, wherein the segmentation process is carried out in two steps, with the area which has marking contrast agent being segmented in the first step and having an edge area added to it in the second step in order to include the wall of the hollow organ.

5. The method as claimed in claim 1, wherein, during the three-dimensional edge detection process, variances are calculated in at least one of an area and radius around the image voxel for each image voxel in the image data record in the section of interest, in order to determine sudden contrast changes and their spatial orientation, and their tangential planes in the image data record.

6. The method as claimed in claim 5, wherein one-dimensional variances are determined for at least three spatial directions, three of which spatial directions are linearly independent.

7. The method as claimed in claim 6, wherein at least one of canonic axes, surface diagonals and spatial diagonals of any desired cuboid reference volume in the section of interest are used as spatial directions.

8. The method as claimed in claim 5, wherein the tangential planes are covered by the vectors $v_{min}$ and $v_\perp$, with the vector $v_\perp$ being at right angles to a plane which is covered by the vectors $v_{min}$ and $v_{max}$, and with the vector $v_{max}$ pointing in the direction of the greatest magnitude of the variance, and with the vector $v_{min}$ pointing in the direction of the smallest magnitude of the variance.

9. An apparatus, comprising:
an image recording system for recording measurement data for a tomographic 3D image data record of a body area of a patient;
an image processing system for reconstruction of the 3D image data record from the measurement data from the image recording system, the image processing system including an image post-processing module for,
carrying out an automatic three-dimensional edge detection process, at least in a section of interest of a 3D image data record covering a hollow organ at least partially filled with marking contrast agent and with basic contrast agent, to determine at least transitions between areas which include marking contrast agent and one wall of the hollow organ in the image data record as boundary surfaces,
carrying out a weighted high-pass filtering process at right angles to the boundary surfaces which leads to removal at the areas including marking contrast agent, process areas around the transitions being given a relatively lower weighting than areas relatively further away from the transitions, and
carrying out a low-pass filtering process in the areas around the transitions, to smooth the transitions.

10. The apparatus as claimed in claim 9, wherein the image post-processing module is designed such that, during the three-dimensional edge detection process, transitions between areas including marking contrast agent and areas containing basic contrast agent, between areas containing basic contrast agent and the wall of the hollow organ, and between areas containing basic contrast agent and the wall of the hollow organ, are also determined as boundary surfaces in the image data record.

11. The apparatus as claimed in claim 9, wherein the image post-processing module is designed to segment the hollow organ in the 3D image data record to obtain the section of interest in the image data record for the automatic three-dimensional edge detection process.

12. The apparatus as claimed in claim 11, wherein the image post-processing module is designed to carry out the segmentation process in two steps, with the area including marking contrast agent being segmented in a first step and having an edge area added to it in the second step, in order to include the wall of the hollow organ.

13. The apparatus as claimed in claim 9, wherein the image post-processing module is designed to, during the three-dimensional edge detection process, calculate variances in at least one of a predetermined area and radius around the image voxel for each image voxel in the image data record in the section of interest, to determine sudden contrast changes and their spatial orientation, and their tangential planes in the image data record.

14. The apparatus as claimed in claim 13, wherein the image post-processing module is designed to determine one-dimensional variances for at least three spatial directions, three of which spatial directions are linearly independent.

15. The apparatus as claimed in claim 14, wherein the image post-processing module is designed to use at least one of canonic axes, surface diagonals and spatial diagonals of any desired cuboid reference volume in the section of interest as spatial directions.

16. The apparatus as claimed in claim 13, wherein the image post-processing module is designed to cover the tangential planes by the vectors $v_{min}$ and $v_\perp$, with the vector $v_\perp$ being at right angles to a plane which is covered by the vectors $v_{min}$ and $v_{max}$, and with the vector $v_{max}$ pointing in the direction of the greatest magnitude of the variance, and with the vector $v_{min}$ pointing in the direction of the smallest magnitude of the variance.

17. The method as claimed in claim 1, wherein the method is for virtual colonography.

18. The method as claimed in claim 1, wherein, during the three-dimensional edge detection process, transitions between areas including marking contrast agent and areas containing basic contrast agent, and transitions between areas which have marking contrast agent, and between areas containing basic contrast agent and the wall of the hollow organ, are also determined as boundary surfaces in the image data record.

19. The method as claimed in claim 2, wherein, during the three-dimensional edge detection process, variances are calculated in at least one of an area and radius around the image voxel for each image voxel in the image data record in the section of interest, in order to determine sudden contrast changes and their spatial orientation, and their tangential planes in the image data record.

20. The method as claimed in claim 19, wherein one-dimensional variances are determined for at least three spatial directions, three of which spatial directions are linearly independent.

21. The method as claimed in claim 20, wherein at least one of canonic axes, surface diagonals and spatial diagonals of any desired cuboid reference volume in the section of interest are used as spatial directions.

22. The method as claimed in claim 6, wherein the tangential planes are covered by the vectors $v_{min}$ and $v_\perp$, with the vector $v_\perp$ being at right angles to a plane which is covered by the vectors $v_{min}$ and $v_{max}$, and with the vector $v_{max}$ pointing in the direction of the greatest magnitude of the variance, and with the vector $v_{min}$ pointing in the direction of the smallest magnitude of the variance.

23. The method as claimed in claim 7, wherein the tangential planes are covered by the vectors $v_{min}$ and $v_\perp$, with the vector $v_\perp$ being at right angles to a plane which is covered by the vectors $v_{min}$ and $v_{max}$, and with the vector $v_{max}$ pointing in the direction of the greatest magnitude of the variance, and with the vector $v_{min}$ pointing in the direction of the smallest magnitude of the variance.

24. The apparatus as claimed in claim 10, wherein the image post-processing module is designed to segment the hollow organ in the 3D image data record to obtain the section of interest in the image data record for the automatic three-dimensional edge detection process.

25. The apparatus as claimed in claim 10, wherein the image post-processing module is designed to, during the three-dimensional edge detection process, calculate variances in at least one of a predetermined area and radius around the image voxel for each image voxel in the image data record in the section of interest, to determine sudden contrast changes and their spatial orientation, and their tangential planes in the image data record.

26. The apparatus as claimed in claim 25, wherein the image post-processing module is designed to determine one-dimensional variances for at least three spatial directions, three of which spatial directions are linearly independent.

27. The apparatus as claimed in claim 26, wherein the image post-processing module is designed to use at least one of canonic axes, surface diagonals and spatial diagonals of any desired cuboid reference volume in the section of interest as spatial directions.

28. A system for post-processing of a 3D image data record of at least one hollow organ which is at least partially filled with marking contrast agent and with basic contrast agent, recorded via an imaging tomographic appliance, the system comprising:

means for carrying out an automatic three-dimensional edge detection process, at least in one section of the image data record of interest and covering the hollow organ which is filled with contrast agent, to determine at least transitions between areas including marking contrast agent and one wall of the hollow organ in the image data record as boundary surfaces;

means for carrying out a weighted high-pass filtering process at right angles to the boundary surfaces and leads to removal of the areas including contrast agent, process areas around the transitions being given a relatively lower weighting than areas relatively further away from the transitions; and means for carrying out a low-pass filtering process in the areas around the transitions, to smooth the transitions.

* * * * *